US012575740B2

(12) United States Patent     (10) Patent No.:   US 12,575,740 B2
Lee et al.     (45) Date of Patent:    Mar. 17, 2026

(54) BODY EXTREMITY TEMPERATURE CHANGE MONITORING SYSTEM AND METHOD

(71) Applicant: PUKYONG NATIONAL UNIVERSITY INDUSTRY-UNIVERSITY COOPERATION FOUNDATION, Busan (KR)

(72) Inventors: Byeong Il Lee, Busan (KR); Myung Gi Yi, Busan (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 95 days.

(21) Appl. No.: 18/646,830

(22) Filed: Apr. 26, 2024

(65) Prior Publication Data

US 2024/0358260 A1     Oct. 31, 2024

(30) Foreign Application Priority Data

Apr. 27, 2023    (KR) ........................ 10-2023-0055754

(51) Int. Cl.
    *A61B 5/00*       (2006.01)
    *A61B 5/01*       (2006.01)
    *G06T 7/11*       (2017.01)

(52) U.S. Cl.
    CPC .............. *A61B 5/015* (2013.01); *A61B 5/004* (2013.01); *G06T 7/11* (2017.01); *A61B 2576/02* (2013.01); *G06T 2207/30004* (2013.01)

(58) Field of Classification Search
    CPC ..... A61B 5/015; A61B 5/004; A61B 2576/02; G06T 7/11; G06T 2207/30004
    See application file for complete search history.

(56) References Cited

U.S. PATENT DOCUMENTS

2014/0148705 A1*   5/2014   Linne ...................... A61B 5/70
                                         600/474

FOREIGN PATENT DOCUMENTS

KR         10-1519469 B1     5/2015

* cited by examiner

*Primary Examiner* — Keith M Raymond
*Assistant Examiner* — Adam D. Kolkin
(74) *Attorney, Agent, or Firm* — Han's Law Office

(57) ABSTRACT

The present disclosure relates to a body extremity temperature change monitoring system and method. More specifically, the present disclosure relates to a body extremity temperature change monitoring system and method, which can monitor a temperature change by recognizing a body extremity and measuring the body temperature of the recognized body extremity. The body extremity temperature change monitoring system comprises: an image data acquisition unit that acquires body extremity image data including a hand or a foot; a segmented area generation unit; and a body extremity temperature map generation unit that generates a body extremity temperature map using temperature data for each of the segmented areas, wherein the body extremity is defined to include base parts having a palm and a foot sole, and branch parts having fingers and toes.

16 Claims, 15 Drawing Sheets

BODY TEMPERATURE CHANGE
MAP GENERATION MODULE

171

STATE CHANGE INFERENCE MODULE

173

S17

GENERATE BODY TEMPERATURE
CHANGE MAP — S171

INFER STATE CHANGE — S173

1   2   3   4   5

1    2    3    4    5

BODY EXTREMITY TEMPERATURE CHANGE MONITORING SYSTEM AND METHOD

CROSS-REFERENCE TO RELATED APPLICATION

This application claims priority to and the benefit of Korean Patent Application No. 10-2023-0055754 filed on Apr. 27, 2023, in the Korean Intellectual Property Office, the entire disclosure of which is incorporated herein by reference.

BACKGROUND

1. Field

The present disclosure relates to a body extremity temperature change monitoring system and method. More specifically, the present disclosure relates to a body extremity temperature change monitoring system and method, which can monitor a body temperature change by measuring body temperatures before and after treatment for a body extremity and analyzing the measurement results.

2. Description of the Related Art

Recently, the market for personal healthcare devices to continuously monitor an individual's health has been growing explosively. The healthcare devices encompass wearable devices represented by smart watches. In addition, there are also health management pillows for monitoring an individual's sleeping condition, etc.

When a patient receives treatment at a medical institution such as an oriental medicine clinic or an orthopedic clinic, the treatment is generally performed while lying or in a prone position on a bed.

Treatment at such a medical institution generally has the effect of relaxing body muscles or facilitating blood circulation. The effects of the aforementioned treatment are difficult to show as standardized results, and there is a difficulty in confirming the effectiveness of the abovementioned treatment by receiving feedback on how a patient feels after the treatment is completed.

Korean Patent No. 10-1519469 (May 6, 2015) discloses a conventional health monitoring pillow.

SUMMARY

The present disclosure provides a body extremity temperature change monitoring system and method, which can monitor a temperature change by recognizing a body extremity and measuring the body temperatures of the recognized body extremity.

A body extremity temperature change monitoring system according to an embodiment of the present disclosure may include: an image data acquisition unit that acquires body extremity image data, which is image data of a body extremity including a hand or a foot; a segmented area generation unit that segments the body extremity image data according to a preset reference to generate two or more segmented areas; and a body extremity temperature map generation unit that generates a body extremity temperature map using temperature data for each of the segmented areas, wherein the body extremity is defined to include base parts having a palm and a foot sole, and branch parts having fingers and toes.

The image data acquisition unit may include: an image data acquisition module that acquires image data of the body extremity; and a thermal image data acquisition module that acquires thermal image data of the body extremity.

The segmented area generation unit may include: a body extremity type classification module that identifies the type of the body extremity; and an area segmentation module that generates at least two segmented areas using the preset reference according to the body extremity type.

The body extremity type classification module may acquire a boundary line for the body extremity using the body extremity image data and may compare the average length of the branch parts with the average length of the base parts, to classify a body extremity type into a hand or a foot according to the preset reference.

When the body extremity type is a hand, the preset reference may include any one of 24-area segmentation, 32-area segmentation, and 5-line segmentation, and when the body extremity type is a foot, the preset reference may include any one of 19-area segmentation and 5-line segmentation.

The body extremity temperature map generation unit may include: an image data merge module that generates merged image data by mapping the thermal image data to the image data including the segmented areas; and a body temperature distribution data generation module that generates the body extremity temperature map, which is temperature data for each of the segmented areas, using the merged image data.

The body extremity temperature map may be acquired at a preset period to be generated to include time-series information.

The system may further include a body temperature change analysis unit that observes a user's body temperature change using the body extremity temperature map and infers a user's state change according to the body temperature change using the preset reference.

The body temperature change analysis unit may include: a body temperature change map generation module that calculates the user's body temperature change for a preset time using the body extremity temperature map and generates a body temperature change map using the body temperature change for each of the segmented areas; and a state change inference module that compares a preset body temperature change reference with the body temperature change map to perform defining on the user's state change.

A body extremity temperature change monitoring method according to another embodiment of the present disclosure may include: an image data acquisition step of, by using an image data acquisition unit, acquiring body extremity image data that is image data of a body extremity including a hand or a foot; a segmented area segmentation step of, by using a segmented area generation unit, segmenting the body extremity image data according to the preset reference to generate two or more segmented areas; and a body extremity temperature map generation step of, by using a body extremity temperature map generation unit, generating a body extremity temperature map using temperature data for each of the segmented areas, wherein the body extremity is defined to include base parts having a palm and a foot sole, and branch parts having fingers and toes.

The image data acquisition step may include: acquiring image data of the body extremity; and acquiring thermal image data of the body extremity.

The segmented area generation step may include: identifying a body extremity type; and generating two or more segmented areas using the preset reference according to the body extremity type.

In the step of classifying a body extremity type, a boundary line for the body extremity may be acquired using the body extremity image data, and the body extremity type may be classified into a hand or a foot according to the preset reference by comparing the average length of the branch parts with the average length of the base parts.

When the body extremity type is a hand, the preset reference may include any one of 24-area segmentation, 32-area segmentation, and 5-line segmentation, and when the body extremity type is a foot, the preset reference may include any one of 19-area segmentation and 5-line segmentation.

The body extremity temperature map generation step may include: an image data merging step of generating merged image data by mapping the thermal image data to the image data including the segmented areas; and a body temperature distribution generation step of generating the body extremity temperature map, which is temperature data for each of the segmented areas, using the merged image data.

The body extremity temperature map may be acquired at a preset period to be generated to include time-series information.

The method may further include observing the user's body temperature change using the body extremity temperature map in a body temperature change analysis unit, and analyzing the body temperature change by inferring a user's state change according to the body temperature change using the preset reference.

The method may further include: calculating the user's body temperature change for a preset time using the body extremity temperature map, and generating a body temperature change map using the body temperature change for each of the segmented areas; and comparing the body temperature change map with a preset body temperature change reference to define a change in the user's state.

BRIEF DESCRIPTION OF DRAWINGS

FIG. 5 is a block diagram of a body temperature change analysis unit in the body extremity temperature change monitoring system of FIG. 1.

DETAILED DESCRIPTION

Figure 1:
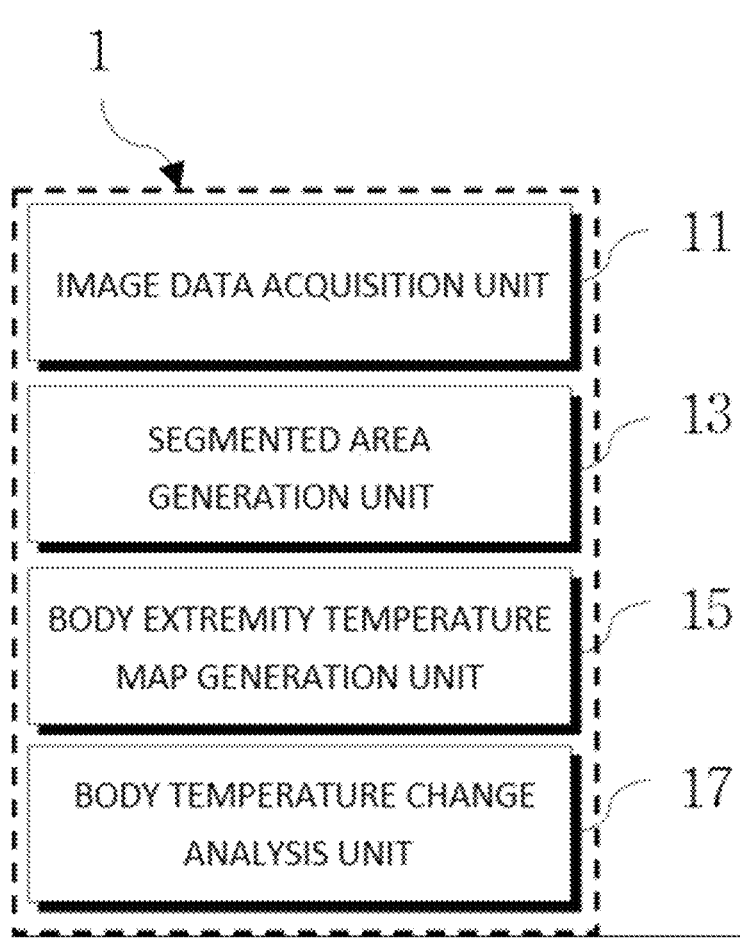
FIG. 1 is a block diagram showing a body extremity temperature change monitoring system according to an embodiment of the present disclosure.

Hereinafter, embodiments of the present disclosure are described in detail with reference to illustrative drawings. In various different drawings, the same components are designed with the same or similar reference numerals and detailed descriptions thereof may be omitted. In addition, as to known configurations or functions, reference is made to known technologies and detailed descriptions thereof may be omitted. Throughout the specification, when the terms "include", "comprise", "have", "consist of", etc. are used, unless "only ~" is used, other components may be added. When a component is expressed in the singular form, plural forms may also be included, unless clearly indicated otherwise.

In addition, in describing the components of the present disclosure, terms such as first, second, A, B, (a), and (b) may be used. These terms are only used to distinguish the components from other components, and the natures, sequences, orders, or numbers of the components are not limited by these terms.

In describing the positional relationship of components, when two or more components are described as being "linked," "coupled," or "connected," etc., two or more components may be directly "linked," "coupled," or "connected," but it should be understood that other components different from the two or more components may be further "interposed" to be "linked," "coupled," or "connected". Here, the other components may also be included in one or more of the two or more components that are "linked," "coupled," or "connected" to each other.

In explaining temporal flow relationships related to components, operation methods, manufacturing methods, etc., for example, temporal precedence relationships such as "after ~", "subsequent to ~", "following ~", "before ~", etc. or in describing sequential relationships, unless the term "immediately" or "directly" is used, cases of being non-continuous may also be included.

Meanwhile, when numerical values or corresponding information about a component (e.g. level, etc.) are mentioned, unless separately explicitly stated, the numerical values or the information corresponding thereto can be interpreted as including error ranges that may occur due to various factors (e.g., process factors, internal or external shocks, noises, etc.).

In addition, the technical features described in the body extremity temperature change monitoring system can also be applied to the body extremity temperature change monitoring method, and the reverse is also true.

Figure 2:
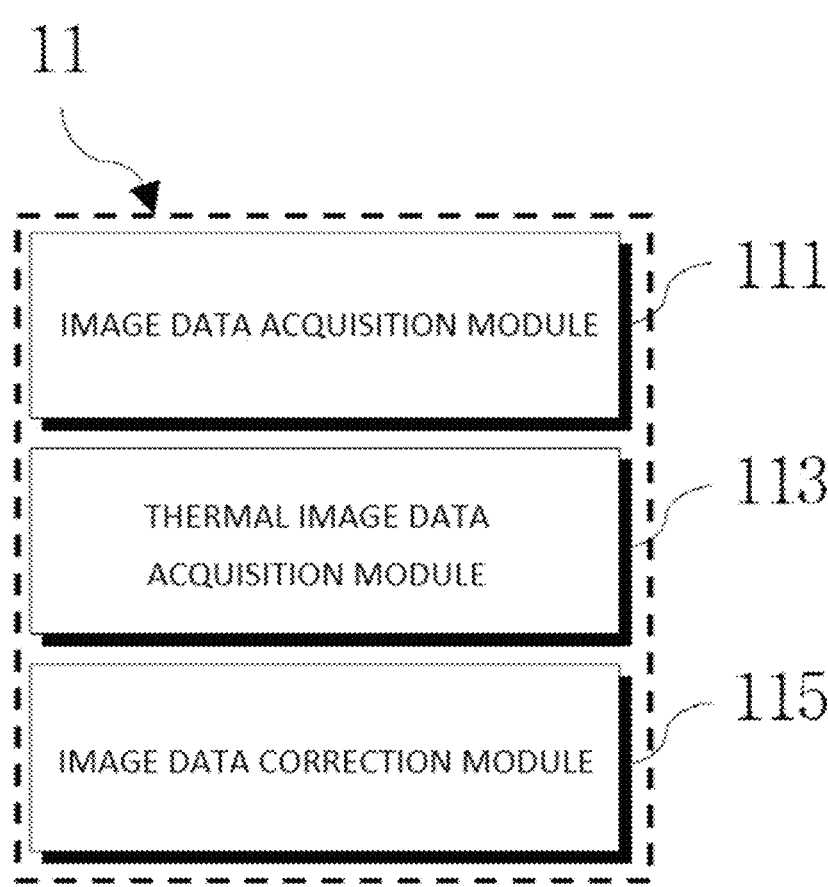
FIG. 2 is a block diagram of an image data acquisition unit in the body extremity temperature change monitoring system of FIG. 1.
Figure 3:
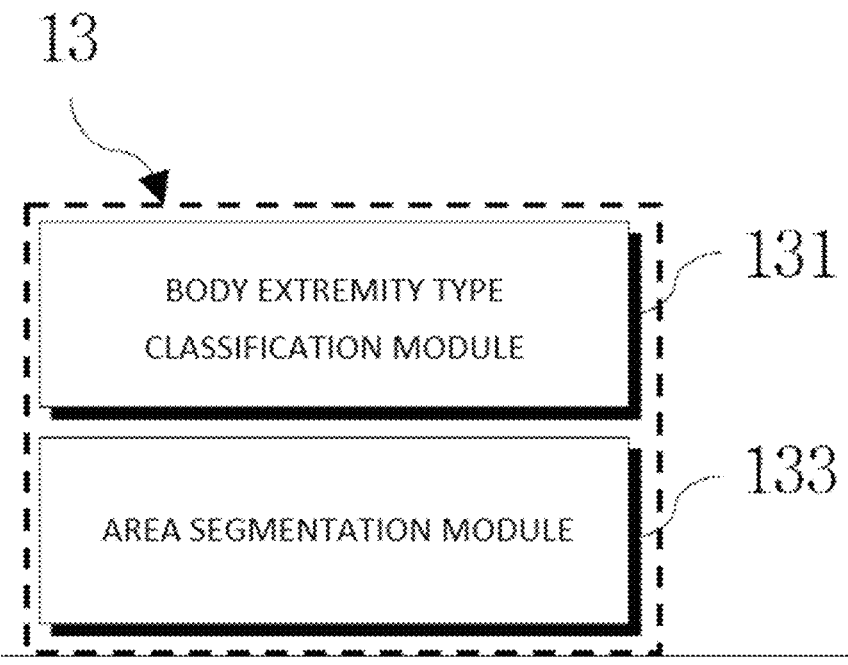
FIG. 3 is a block diagram of a segmented area generation unit in the body extremity temperature change monitoring system of FIG. 1.
Figure 4:
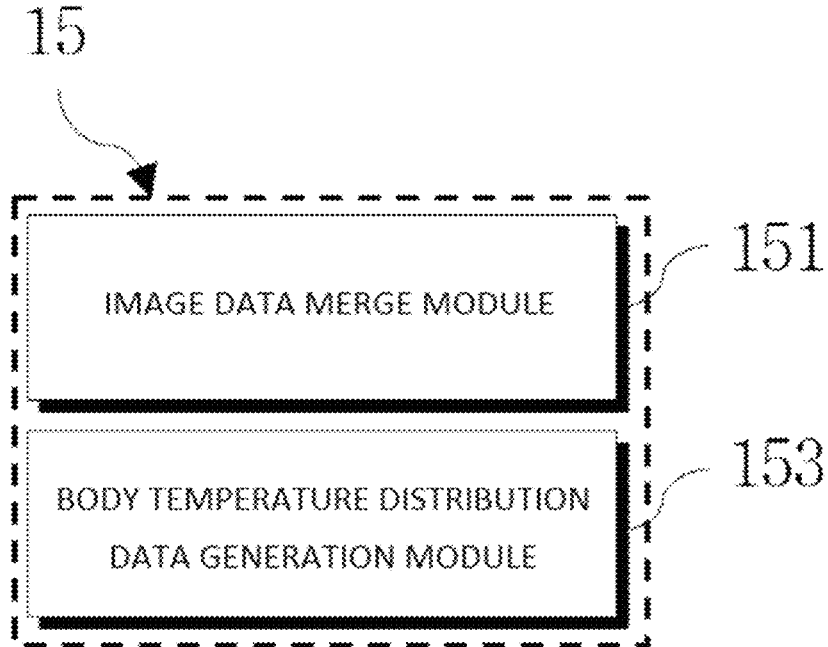
FIG. 4 is a block diagram of a body extremity temperature map generation unit in the body extremity temperature change monitoring system of FIG. 1.
Figure 5:
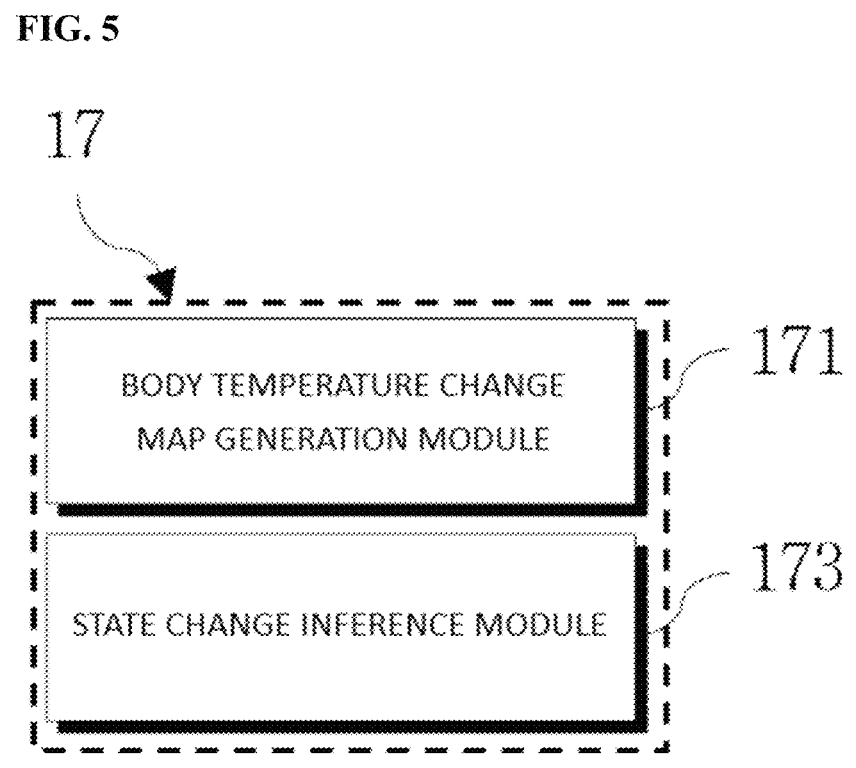

FIG. 1 is a block diagram showing a body extremity temperature change monitoring system 1 according to an embodiment of the present disclosure, FIG. 2 is a block diagram of an image data acquisition unit, FIG. 3 is a block diagram of a segmented area generation unit, FIG. 4 is a block diagram of a body extremity temperature map generation unit, and FIG. 5 is a block diagram of a body temperature change analysis unit.

Hereinafter, referring to FIGS. 1 to 5, a body extremity temperature change monitoring system (for brevity, to be referred to as a monitoring system, hereinafter) according to an embodiment of the present disclosure will be described in detail.

Referring to the drawings, the monitoring system 1 is configured to measure the body temperature on a body extremity of a user (treatment subject), generate a temperature distribution map using the measured body temperature, and monitor a body temperature change in the user's body extremity using the generated temperature distribution map. To this end, as shown in FIG. 1, the monitoring system 1 of the present disclosure may include an image data acquisition unit 11, a segmented area generation unit 13, and a body extremity temperature map generation unit 15.

The image data acquisition unit 11 is configured to acquire the body extremity image data, which is image data of a body extremity including a hand or a foot. Here, the body extremity may include base parts having a palm and a foot sole, and branch parts having fingers and toes. The image data acquisition unit 11 may be formed to include an image data acquisition module 111 and a thermal image data acquisition module 113, as shown in FIG. 2.

The image data acquisition module 111 may be configured to acquire image data of the body extremity. Here, the image data may be an image acquired using a device such as a video camera, and the image data may be acquired at a preset period.

The thermal image data acquisition module 113 may be configured to acquire thermal image data of the body extremity. Here, thermal image data may be thermal image data acquired using a device such as a thermal imaging camera, and thermal image data may be acquired at a preset period.

Meanwhile, the image data acquisition unit 11 may further include an image data correction module 115, as necessary. The image data correction module 115 may be configured to correct distortion of image data and thermal image data. In the present disclosure, in order to allow the image data to be used without an error, the most desirable way in acquiring image data and thermal image data is to perform photographing perpendicular to the hands or feet of all photographed subjects so that the distances between the camera and all the hands or feet are constant. However, in general, in using this configuration, there are problems in that the location of a camera that photographs image data and thermal image data may be limited and the location may change depending on the movement of a user.

Therefore, the image data correction module 115 according to an embodiment of the present disclosure may be configured to acquire image data and thermal image data and performs correction for distortion or difference in the image data and thermal image data using a preset algorithm. By using this, the image data acquired in the present disclosure may always be provided as data having the same distortion and/or difference corrected.

When the image data is acquired, the segmented area generation unit 13 may be configured to generate at least two segmented areas by segmenting the body extremity image data according to the preset reference. To this end, as shown in FIG. 3, the segmented area generation unit 13 may include a body extremity type classification module 131 and an area segmentation module 133.

The body extremity type classification module 131 may be configured to identify a body extremity type. As described above, in the present disclosure, the body extremity may be defined as either a hand or a foot. Accordingly, the body extremity type classification module 131 may be configured to determine and classify the type of a body portion included in the image data, whether the base part is a hand or a foot.

In one embodiment of the present disclosure, the body extremity type classification module 131 may be configured to acquire a boundary line for the body extremity using the body extremity image data and compares the average length of the branch parts with the average length of the base parts, to classify a body extremity type into a hand or a foot according to the preset reference.

In the case of a hand of a human body, there is no big difference between the length of the palm and the lengths of fingers. However, in the case of a foot of a human body, there is a big difference between the length of the foot sole and the lengths of toes. Therefore, the body extremity type classification module 131 according to an embodiment of the present disclosure may be configured such that after obtaining the boundary of the body extremity using such characteristics of a hand or foot, it is determined whether the body extremity included in the image is a hand or a foot by comparing the length of the body extremity and the base part.

The area segmentation module 133 may be configured to generate at least two segmented areas using the preset reference depending on the body extremity type. By using the preset reference, the area segmentation module 133 may generate a plurality of segmented areas for the video image of a hand or may generate a plurality of segmented areas for the video image of a foot.

In the body extremity type classification module 131, if the body extremity included in the image data are determined to be a hand, the area segmentation module 133 obtains a preset reference for segmenting a hand area. Here, the preset reference for hand area segmentation may be any one of 24-area segmentation, 32-area segmentation, and 5-line segmentation.

Figure 11:
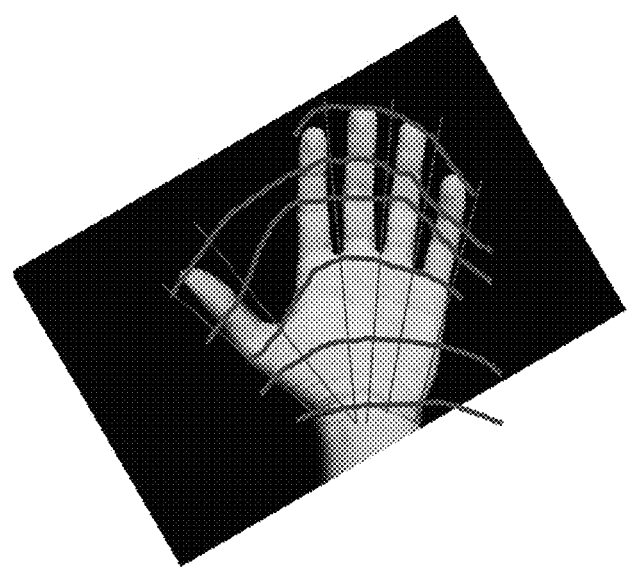
FIGS. 11 to 13 show examples of 24-area segmentation for a hand, according to an embodiment of the present disclosure.
Figure 12:
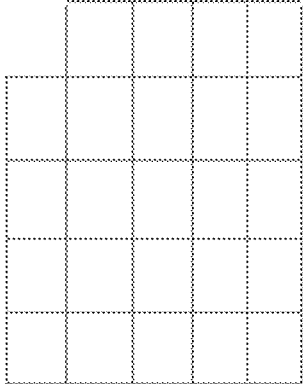
Figure 13:
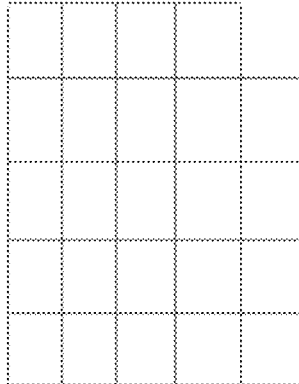

FIGS. 11 to 18 show preset references for segmenting a hand area. In an embodiment of the present disclosure, area segmentation for a hand may be basically performed on the entire palm based on the branch parts (fingers). FIGS. 11 to 13 show examples of 24-area segmentation for a hand, according to an embodiment of the present disclosure. FIGS. 12 and 13 show segmented areas for the left and right hands, respectively.

The preset references of FIGS. 11 to 13 are for generating a total of 24 areas are generated based on the body extremity. Here, segmented areas are generated for each finger in the lengthwise direction based on finger knuckles, and for the base part of the palm, segmented areas are generated in the traverse direction based on the areas extending from the segmented areas for the fingers. The 24-area segmentation may allow the respective segmented areas to be distinguished from each other by performing numbering or coloring on the respective segmented areas.

Figure 14:
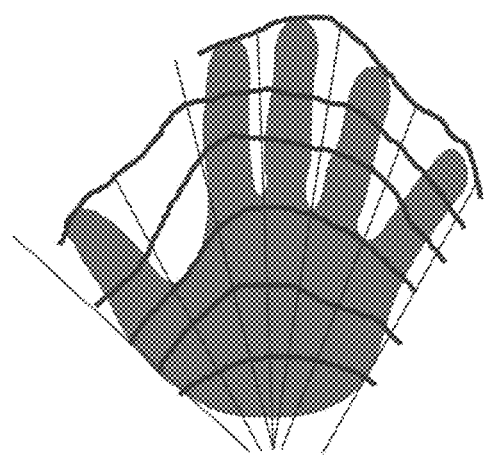
FIGS. 14 to 16 show examples of 32-area segmentation in the hand segmented areas according to an embodiment of the present disclosure.
Figure 15:
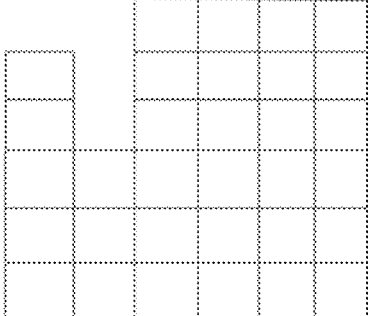
Figure 16:
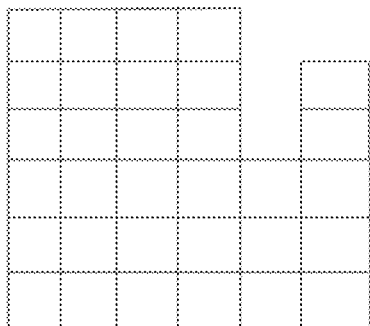

FIGS. 14 to 16 show examples of 32-area segmentation for a hand, according to an embodiment of the present disclosure. FIGS. 15 and 16 show segmented areas for the left and right hands, respectively. The preset references of FIGS. 14 to 16 are examples for performing a more specific analysis on a wider area (a palm that meets the index finger) than other areas among the 24 areas in FIG. 11.

Here, assuming that a virtual finger exists between the thumb and the index finger, a total of 6 vertical references are set, and segmented areas are generated horizontally based on the finger knuckles and lines that segment the palm into three segments. Since the virtual finger is an area where a body temperature is not actually measured, no segmented area is generated in the area where the virtual finger exists. The 32-area segmentation may allow the respective segmented areas to be distinguished from each other by performing numbering or coloring on the respective segmented areas.

Figure 17:
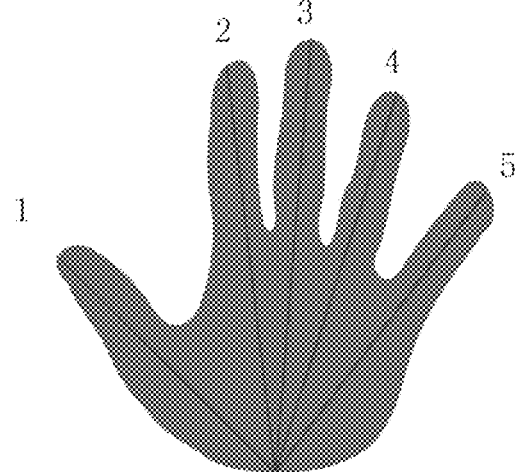
FIGS. 17 and 18 show examples of 5-line segmentation for a hand, according to an embodiment of the present disclosure.
Figure 18:
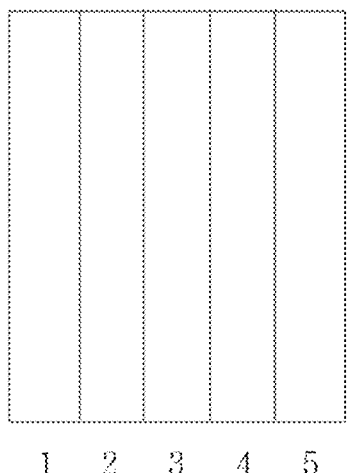

FIGS. 17 and 18 show examples of 5-line segmentation for a hand, according to an embodiment of the present disclosure. FIG. 18 shows an embodiment of segmenting areas for the left or right hand. The preset references of FIGS. 17 and 18 are references in which 5-line areas are generated using the lines that connect the tips of the respective fingers with the center point of the wrist, and the 5-line segmentation may allow the respective segmented areas to be distinguished from each other by performing numbering or coloring on the respective segmented areas.

Meanwhile, the area segmentation module 133 obtains a preset reference for segmenting a foot area. Here, the preset reference for hand-area segmentation may be any one of 19-area segmentation and 5-line segmentation.

Figure 19:
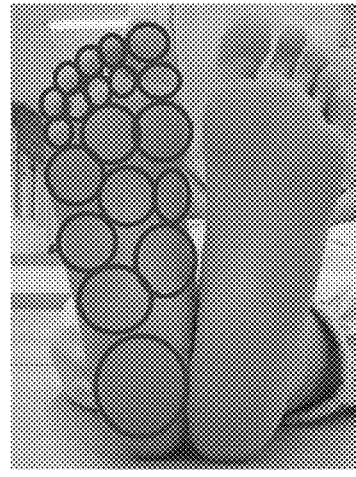
FIGS. 19 and 20 show examples of 19-area segmentation for a foot, according to an embodiment of the present disclosure.
Figure 20:
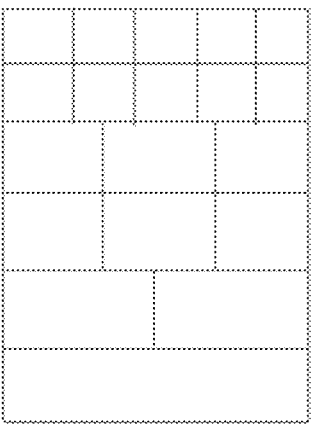

FIGS. 19 to 22 show preset references for segmenting a foot area. FIGS. 19 and 20 show examples of 19-area segmentation for a foot, according to an embodiment of the present disclosure. FIG. 20 shows an embodiment of segmenting areas for left and right feet. The preset reference of FIG. 19 is a reference in which by using the respective knuckles, two segmented areas are generated in the body extremity and nine segmented areas are generated on the foot sole, and in the foot sole, one area is formed at a heel portion, two areas are formed at the upper side of the heel portion, and three areas are then formed between toes and the two areas in a total of two rows. The 19-area segmentation may be configured to distinguish the respective segmented areas from each other by performing numbering or coloring on the respective segmented areas.

Figure 21:
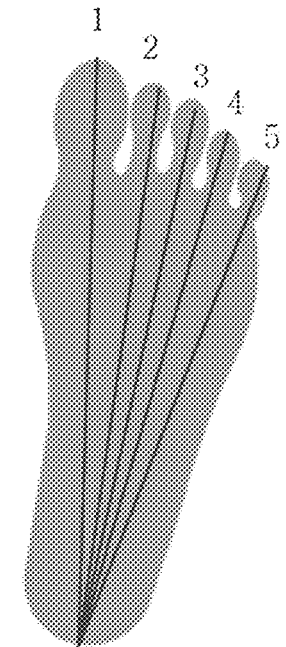
FIGS. 21 and 22 show examples of 5-line segmentation for a foot, according to an embodiment of the present disclosure.
Figure 22:
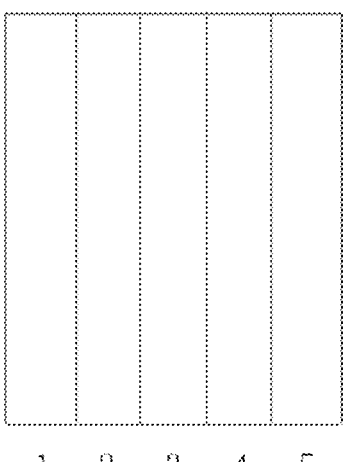

In addition, FIGS. 21 and 22 show examples of 5-line segmentation for a foot, according to an embodiment of the present disclosure. FIG. 22 shows an embodiment of segmenting areas for a left or right foot. The 5-line segmentation of FIG. 21, similar to FIG. 17, is performed such that segmented areas are generated based on 5 lines connecting the tips of toes and the center point of a heel, and the 5-line segmentation may allow the respective segmented areas to be distinguished from each other by performing numbering or coloring on the respective segmented areas.

When segmented areas are generated for the body extremity obtained as image data, the body extremity temperature map generation unit 15 generates a body extremity temperature map using the temperature data for the respective segmented areas. To this end, the body extremity temperature map generation unit 15 may include an image data merge module 151 and a body temperature distribution data generation module 153, as shown in FIG. 4.

The image data merge module 151 is configured to generate merged image data by mapping thermal image data to the image data including the segmented areas. In one embodiment of the present disclosure, the image data and the thermal image data may be acquired from the image data acquisition unit 11, respectively. In addition, the segmented area generation unit 13 may identify a body extremity type using the image data and generate the segmented areas using the reference according to the body extremity type. The segmented area generated by the segmented area generation unit 13 and the thermal image data acquired by the thermal image data acquisition module 113 of the image data acquisition unit 11 may be merged into merged image data by the image data merge module 151. Here, the image data merge module 151 may also include numbering or coloring, which is a segmentation reference included in the segmented areas.

The body temperature distribution data generation module 153 may be configured to generate the body extremity temperature map, which is temperature data for each segmented area, by using the merged image data. Here, since image data and thermal image data are acquired at a preset period as described above, the body extremity temperature map generated in the body temperature distribution data generation module 153 may also be obtained at a preset period, which means that the body extremity temperature map may be generated including time-series information.

Meanwhile, the body extremity temperature change monitoring system 1 may further include a body temperature change analysis unit 17, as shown in FIG. 1. The body temperature change analysis unit 17 may observe the user's body temperature change using the body extremity temperature map and infer the user's state change according to the body temperature change using the preset reference. To this end, as shown in FIG. 5, the body temperature change analysis unit 17 may be configured to include a body temperature change map generation module 171 and a state change inference module 173.

The body temperature change map generation module 171 may calculate the user's body temperature change for a preset time using the body extremity temperature map and may generate a body temperature change map using the body temperature change for each segmented area.

The body temperature change map generation module 171 may be configured to calculate body temperature change for each segmented area included in the body extremity temperature map. Here, the body temperature change may be a body temperature change between an initial body extremity temperature map set by an administrator and a final body extremity temperature map, or may be a body temperature change for each body extremity temperature map obtained at a preset cycle based on the initial body extremity temperature map.

In a preferred embodiment of the present disclosure, the body temperature change map generation module 171 may be set to generate a body temperature change map using the body temperature change between the initial body extremity temperature map and the final body extremity temperature map, but the present disclosure is not limited thereto. As described above, the body temperature change map may be generated by obtaining body temperature change values at a preset period.

When the body temperature change map is generated in the body temperature change map generation module 171, the state change inference module 173 of the present disclosure may define a change in the user's state by comparing a preset body temperature change reference and a body temperature change map. The preset body temperature change reference may be an expected body temperature change, which is an expected treatment effect when a specific treatment is performed on the user, or may be a reference for defining the user's health status.

Figure 6:
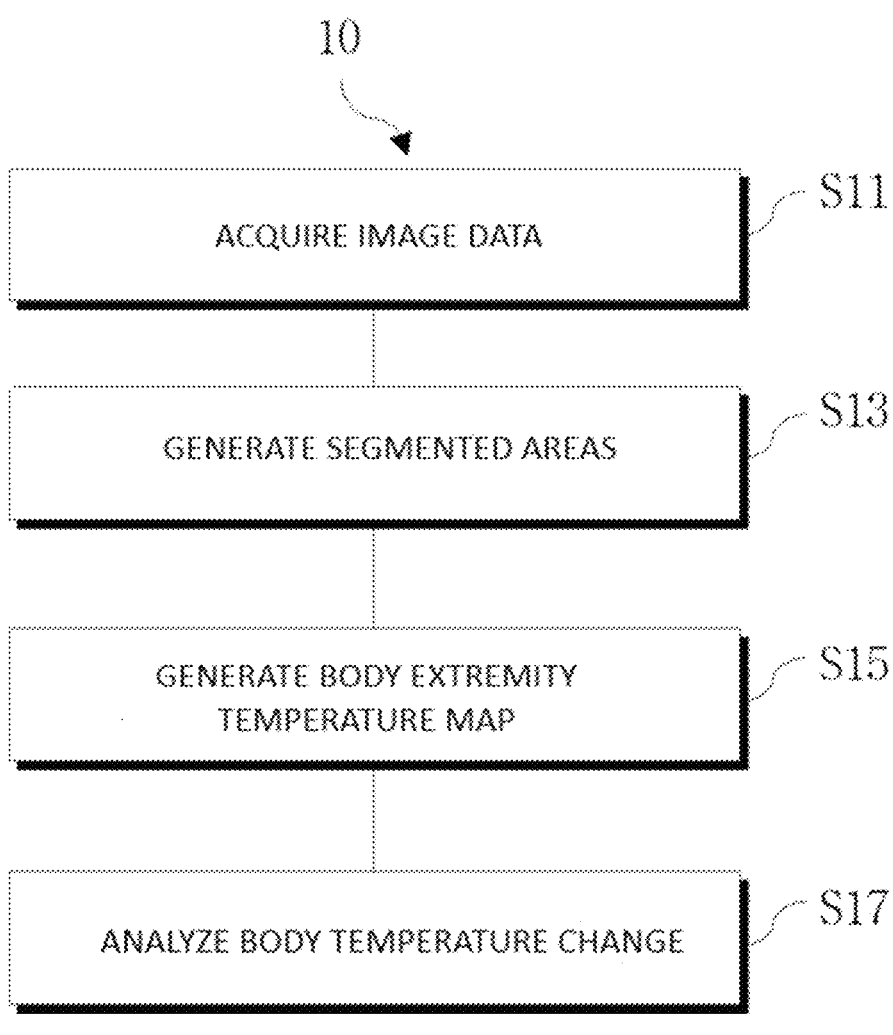
FIG. 6 is a flowchart showing a body extremity temperature change monitoring method according to an embodiment of the present disclosure.
Figure 7:
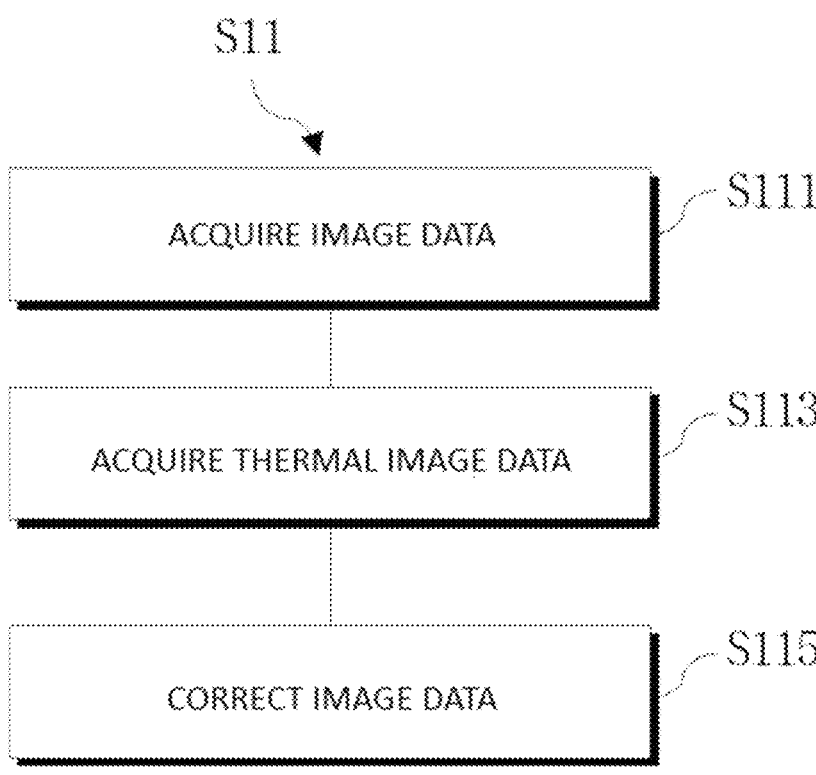
FIG. 7 is a flowchart of step S11 in the body extremity temperature change monitoring method of FIG. 6.
Figure 8:
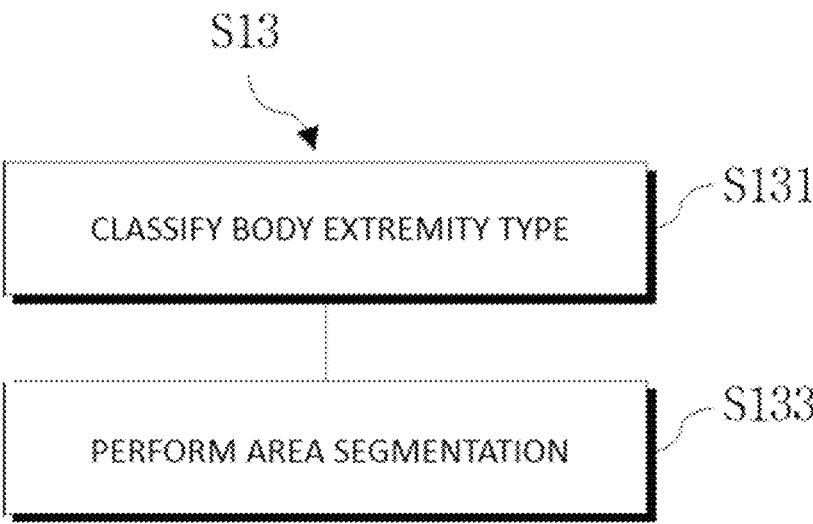
FIG. 8 is a flowchart of step S13 in the body extremity temperature change monitoring method of FIG. 6.
Figure 9:
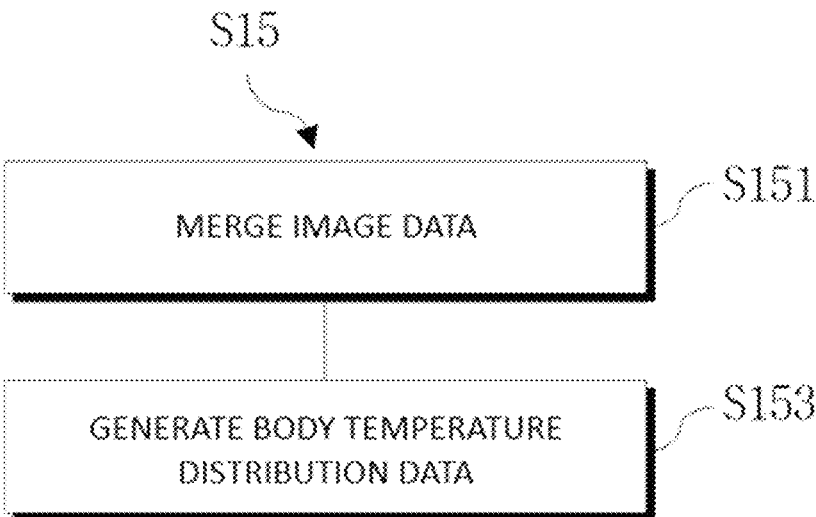
FIG. 9 is a flowchart of step S15 in the body extremity temperature change monitoring method of FIG. 6.
Figure 10:
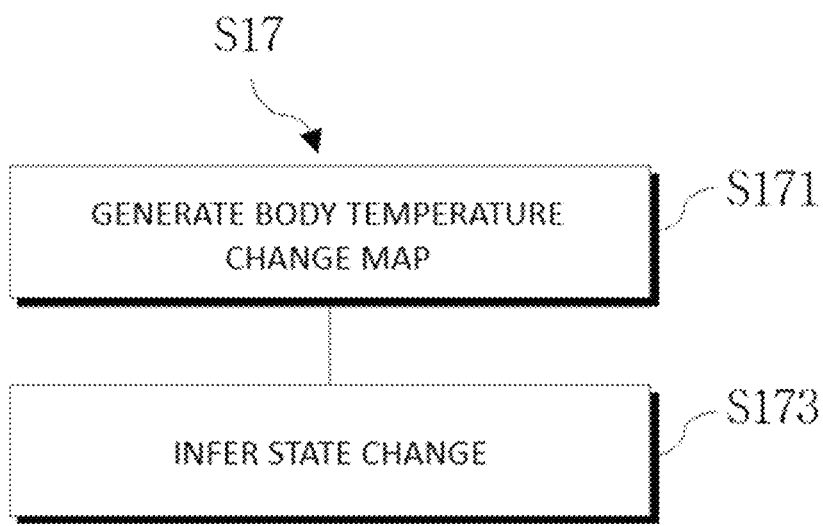
FIG. 10 is a flowchart of step S17 in the body extremity temperature change monitoring method of FIG. 6.

FIGS. 6 to 10 show a method for monitoring a body extremity temperature change according to an embodiment of the present disclosure. FIG. 6 is a flowchart showing a body extremity temperature change monitoring method according to an embodiment of the present disclosure, FIG. 7 is a flowchart of step S11 in the body extremity temperature change monitoring method of FIG. 6, FIG. 8 is a flowchart of step S13, FIG. 9 is a flowchart of step S15, and FIG. 10 is a flowchart of step S17.

Hereinafter, for convenience of explanation, the body extremity temperature change monitoring method of the present disclosure (hereinafter, for brevity, referred to as the monitoring method) is described as using the monitoring system of FIG. 1, but the present disclosure is not limited thereto.

The monitoring method 10 according to an embodiment of the present disclosure is configured to measure the body temperature of a body extremity of a user (a treatment subject), generate a temperature distribution map using the measured body temperature, and monitor body temperature changes of the user's body extremity. To this end, as shown in FIG. 6, the monitoring method 10 according to an embodiment of the present disclosure may include: an image data acquisition step (S11); a segmented area generation step (S13); and a body extremity temperature map generation step (S15).

The image data acquisition step (S11) may be configured to acquire, by using an image data acquisition unit, body extremity image data, which is image data of a body extremity including a hand or a foot. Here, the human body extremities may include base parts including palms and foot soles, and branch parts including fingers and toes. The image data acquisition step (S11) may include the steps of acquiring image data (S111) and acquiring thermal image data (S113), as shown in FIG. 7.

The step of acquiring image data (S111) may be configured to acquire image data of the body extremity. Here, the image data may be an image acquired using a device such as a video camera, and the image data may be acquired at a preset period.

The step of acquiring thermal image data (S113) may be configured to acquire thermal image data of the body extremity. Here, thermal image data may be thermal image data acquired using a device such as a thermal imaging camera, and thermal image data may be acquired at a preset period.

Meanwhile, the step of acquiring image data (S11) may further include a step of correcting the image data (S115), if necessary. The step of correcting image data (S115) may be performed to correct distortion of image data and thermal image data. In the present disclosure, in order to allow the image data to be used without an error, the most desirable way in acquiring image data and thermal image data is to perform photographing perpendicular to the hands or feet of all photographed subjects so that the distances between the camera and all the hands or feet are constant. However, in general, in using this configuration, there are problems in that the location of a camera that photographs image data and thermal image data may be limited and the location may change depending on the movement of a user.

Therefore, the step of correcting image data (S115) may be configured to acquire the image data and the thermal image data and perform correction for distortion and/or differences in the image data and thermal image data by using a preset algorithm. By using this, the image data acquired in the present disclosure may always be provided as data having the same distortion and/or difference corrected.

When the image data is acquired, the segmented area generation step (S13) according to an embodiment of the present disclosure may be configured to segment the body extremity image data according to a preset reference using a segmented area generation unit to generate at least two segmented areas. To this end, in an embodiment of the present disclosure, the segmented area generation step (S13) may include the steps of: classifying a body extremity type (S131); and performing area segmentation (S133), as shown in FIG. 8.

The step of classifying a body extremity type (S131) may be performed to identify the type of a body extremity. As described above, in the present disclosure, the body extremity can be defined as either a hand or a foot. Therefore, the step of classifying a body extremity type (S131), according to an embodiment of the present disclosure may be configured to determine and classify the type of a body portion included in the image data, whether it is a hand or a foot.

In the step of classifying a body extremity type (S131), the boundary line for body extremity may be obtained using the body extremity image data, and the body extremity type may be classified according to the preset reference by comparing the average length of the branch parts with the average length of the base parts.

In the case of a hand of a human body, there is no big difference in the length of the palm and the lengths of fingers. However, in the case of a foot of a human body, there is a big difference in the length of the foot sole and the lengths of toes. Therefore, the step of classifying a body extremity type (S131), according to an embodiment of the present disclosure, may be configured such that after obtaining the boundary of the body extremity using such characteristics of a hand and a foot, it is determined whether the body extremity included in the image is a hand or a foot by comparing the length of the body extremity and the base part.

The step of performing area segmentation (S133) may be configured to generate at least two segmented areas using a preset reference depending on the body extremity type. In the step of performing area segmentation (S133), a plurality of segmented areas for an image of a hand or a plurality of segmented areas for an image of a foot may be generated using the preset reference.

In the step of classifying a body extremity type (S131), if the body extremity included in the image data is classified as a hand, in the step of performing area segmentation (S133), according to an embodiment of the present disclosure, the preset reference for hand area segmentation may be obtained. Here, the preset reference for hand area segmentation may be any one of 24-area segmentation, 32-area segmentation, and 5-line segmentation.

FIGS. 11 to 18 show preset references for hand area segmentation. In one embodiment of the present disclosure, hand area segmentation can be performed on the entire palm based on branch parts (fingers). FIGS. 11 to 13 show examples of 24-area segmentation for a hand. FIGS. 12 and 13 show segmented areas for the left and right hands, respectively.

The preset references in FIGS. 11 to 13 are for generating a total of 24 areas based on a body extremity. Here, segmented areas are generated for each finger in the lengthwise direction based on finger knuckles, and for the base part of the palm, segmented areas are generated in the traverse direction based on the areas extending from the segmented areas for the fingers. The 24-area segmentation may allow the respective segmented areas to be distinguished from each other by performing numbering or coloring on the respective segmented areas.

FIGS. 14 to 16 show examples of 32-area segmentation for a hand. FIGS. 15 and 16 show segmented areas for the left and right hands, respectively. The preset references in FIGS. 14 to 16 are examples for performing more specific analysis on a wider area (a portion of the palm that meets the index finger) than other areas among the 24 areas of FIG. 11.

Here, assuming that a virtual finger exists between the thumb and the index finger, a total of six vertical references are set, and segmented areas are generated horizontally based on the finger knuckles and lines that segment the palm into three segments. Since the virtual finger is an area where a body temperature is not actually measured, no segmented area is generated in the area where the virtual finger exists. The 32-area segmentation may allow the respective segmented areas to be distinguished from each other by performing numbering or coloring on the respective segmented areas.

FIGS. 17 and 18 show examples of 5-line segmentation for a hand, according to an embodiment of the present disclosure. FIG. 18 shows an embodiment of segmenting areas for the left or right hand. The preset references of FIGS. 17 and 18 are references in which 5-line areas are generated using the lines that connect the tips of the respective fingers with the center point of the wrist, and the 5-line segmentation may allow the respective segmented areas to be distinguished from each other by performing numbering or coloring on the respective segmented areas.

Meanwhile, in the step of step of performing area segmentation (S133), a preset reference for segmenting a foot area is obtained. Here, the preset reference for foot-area segmentation may be any one of 19-area segmentation and 5-line segmentation.

FIGS. 19 to 22 show preset references for segmenting a foot area. FIGS. 19 and 20 show examples of 19-area segmentation for a foot, according to an embodiment of the present disclosure. FIG. 20 shows an embodiment of segmenting areas for left and right feet. The preset reference of FIG. 19 is a reference in which by using the respective knuckles, two segmented areas are generated in the body extremity and nine segmented areas are generated on the foot sole, and in the foot sole, one area is formed at a heel portion, two areas are formed at the upper side of the heel portion, and three areas are then formed between toes and the two areas in a total of two rows. The 19-area segmentation may be configured to distinguish the respective segmented areas from each other by performing numbering or coloring on the respective segmented areas.

In addition, FIGS. 21 and 22 show examples of 5-line segmentation. FIG. 22 shows an embodiment of segmenting areas for a left or right foot. The 5-line segmentation of FIG. 21, similar to FIG. 17, is performed such that segmented areas are generated based on 5 lines connecting the tips of toes and the center point of a heel, and the 5-line segmentation may be configured to distinguish the respective segmented areas from each other by performing numbering or coloring on the respective segmented areas.

When segmented areas are generated for the body extremity obtained as image data, a body extremity temperature map is generated using the temperature data for the respective segmented areas in the body extremity temperature map generation step (S15). To this end, the step of generating a body extremity temperature map (S15) may include the steps of: merging image data (S151); and generating body temperature distribution data (S153), as shown in FIG. 9.

The step of merging image data (S151) may be configured to generate merged image data by mapping thermal image data to the image data including the segmented areas. In one embodiment of the present disclosure, image data and thermal image data may be acquired respectively in the image data acquisition step (S11). In addition, in the segmented area generation step (S13), the body extremity type may be identified using the image data, and segmented areas may be generated using the preset reference according to the body extremity type. The segmented areas generated in the segmented area generation step (S13) and the thermal image data acquired in the step of acquiring thermal image data (S113) may be merged into merged image data. Here, in the step of merging image data (S151), numbering or coloring, which is a segmentation reference included in the segmented areas, may be included in the merged image data.

The step of generating body temperature data (S153) may be configured to generate a body extremity temperature map, which is temperature data for each segmented area using the merged image data. Here, since the image data and the thermal image data are acquired at a preset period, the body extremity temperature map generated in the step of generating body temperature data (S153) may also be acquired at a preset period, which means that the body extremity temperature map may be generated including time-series information.

Meanwhile, the body extremity temperature change monitoring method 10 may further include a body temperature change analysis step (S17), as shown in FIG. 6. In the body temperature change analysis step (S17), the user's body temperature change may be observed by means of a body temperature change analysis unit using the body extremity temperature map, and the user's state change according to the body temperature change may be inferred using the preset reference. To this end, as shown in FIG. 10, the body temperature change analysis step (S17), according to an embodiment of the present disclosure, may include the steps of: generating a body temperature change map (S171) and inferring a state change (S173), as shown in FIG. 10.

The step of generating a body temperature change map (S171) may be configured to calculate a user's body temperature change for a preset time using the body extremity temperature map and generate a body temperature change map using the body temperature change for each of the segmented areas.

The step of generating a body temperature change map (S171) may be configured to calculate body temperature changes for the respective segmented areas included in the body extremity temperature map. Here, the body temperature change may be a body temperature change between an initial body extremity temperature map set by an administrator and a final body extremity temperature map, or may be a body temperature change for each body extremity temperature map obtained at a preset cycle based on the initial body extremity temperature map.

In a preferred embodiment of the present disclosure, the step of generating a body temperature change map (S171) may be set to generate a body temperature change map using the body temperature change between the initial body extremity temperature map and the final body extremity temperature map, but the present disclosure is not limited thereto. As described above, the body temperature change map may be generated by obtaining body temperature change values at a preset period.

When the body temperature change map is generated in the step of generating a body temperature change map (S171), the step of inferring a state change (S173) of the present disclosure may define the user's state change by comparing a preset body temperature change reference with the body temperature change map. The preset body temperature change reference may be an expected body temperature change, which is an expected effect of the treatment when a specific treatment is performed on the user, or may be a reference for defining the user's health status.

According to the present disclosure, body temperature changes for body extremities can be cumulatively stored and compared, to accurately confirm the effectiveness of the treatment performed on a user.

Figure 23:
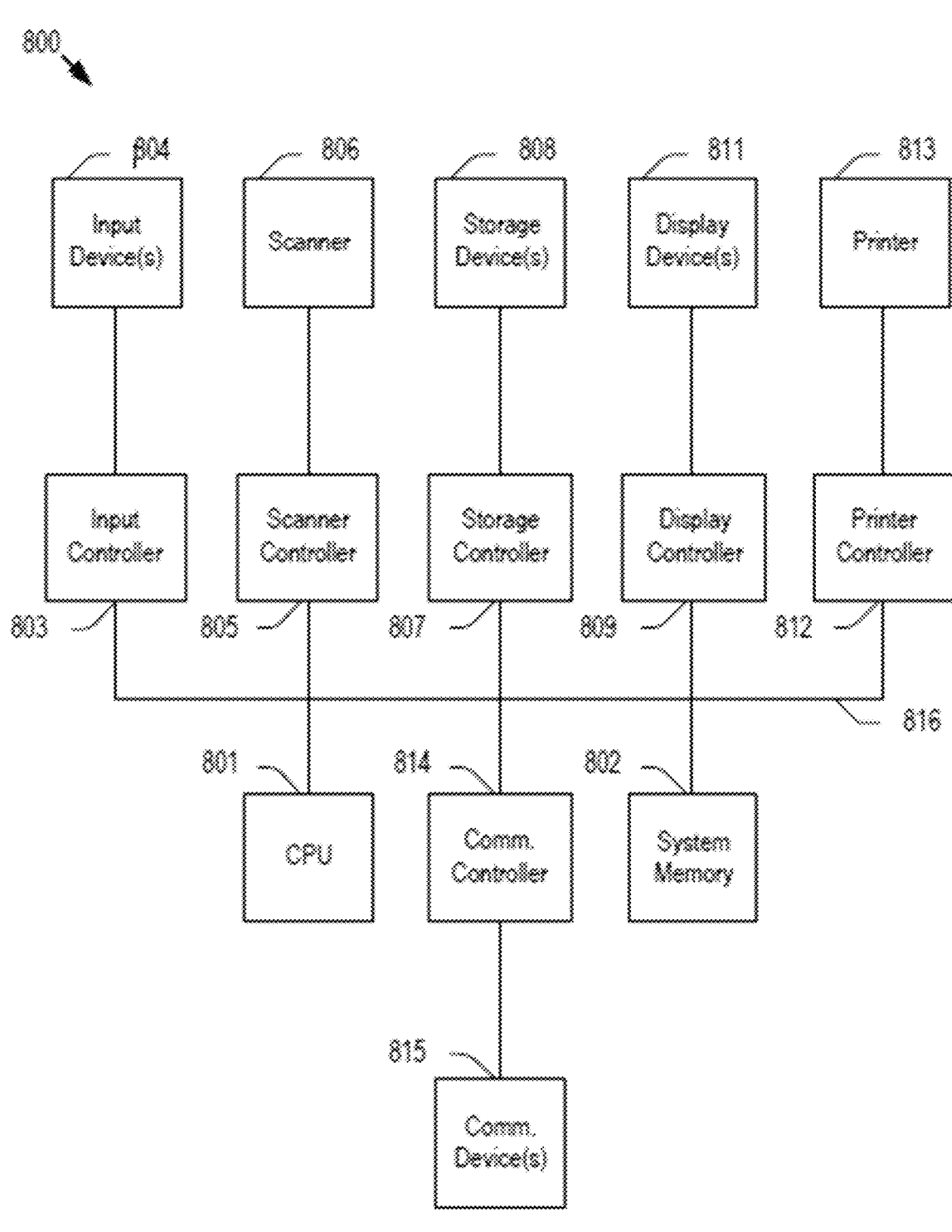
FIG. 23 shows a schematic diagram of a system for implementing one or more aspects of the present disclosure.

FIG. 23 shows a schematic diagram of a system for implementing one or more aspects of the present disclosure. It will be understood that the functionalities shown for system 800 may operate to support various embodiments shown in FIGS. 1 to 5—although it shall be understood that the system may be differently configured and include different components. As illustrated in FIG. 23, the system 800 may include a central processing unit (CPU) 801 that provides computing resources and controls the computer. CPU 801 may be implemented with a microprocessor or the like, and may also include a graphics processor and/or a floating-point coprocessor for mathematical computations. System 800 may also include a system memory 802, which may be in the form of random-access memory (RAM) and read-only memory (ROM).

A number of controllers and peripheral devices may also be provided, as shown in FIG. 23. An input controller 803 represents an interface to various input device(s) 804, such as a keyboard, mouse, or stylus. There may also be a scanner controller 805, which communicates with a scanner 806. System 800 may also include a storage controller 807 for interfacing with one or more storage devices 808 each of which includes a storage medium such as magnetic tape or disk, or an optical medium that might be used to record programs of instructions for operating systems, utilities and applications which may include embodiments of programs that implement various aspects of the present invention. Storage device(s) 808 may also be used to store processed data or data to be processed in accordance with the invention. System 800 may also include a display controller 809 for providing an interface to a display device 811, which may be a cathode ray tube (CRT), a thin film transistor (TFT) display, or other type of display. System 800 may also include a printer controller 812 for communicating with a printer 813. A communications controller 814 may interface with one or more communication devices 815, which enables system 800 to connect to remote devices through any of a variety of networks including the Internet, an Ethernet cloud, an FCOE/DCB cloud, a local area network (LAN), a wide area network (WAN), a storage area network (SAN) or through any suitable electromagnetic carrier signals including infrared signals.

In the illustrated system, all major system components may connect to a bus 816, which may represent more than one physical bus. However, various system components may or may not be in physical proximity to one another. For example, input data and/or output data may be remotely transmitted from one physical location to another. In addition, programs that implement various aspects of this invention may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

The foregoing embodiment is merely an exemplary explanation of the inventive concept of the present disclosure. A person skilled in the art would make various modifications and variations without departing from the essential characteristics of the present disclosure.

Accordingly, the embodiments disclosed in the present disclosure are not intended to limit, but rather to explain, the inventive concept of the present disclosure. In addition, the scope of the inventive concept of the present disclosure is not limited by the embodiments. The scope of protection of the present disclosure should be interpreted in accordance with the appended claims, and all inventive concepts within the equivalent scope should be interpreted as being included in the scope of rights of the present disclosure.

What is claimed is:

1. A body extremity temperature change monitoring system comprising:

an image data acquisition unit that acquires body extremity image data, which is image data of a body extremity including a hand and a foot;

a segmented area generation unit that segments the body extremity image data according to a preset reference to generate two or more segmented areas; and a body extremity temperature map generation unit that generates a body extremity temperature map using temperature data for each of the segmented areas, wherein the body extremity is defined to include base parts having a palm and a foot sole, and branch parts having fingers and toes, wherein the segmented area generation unit comprises a body extremity type classification module that identifies a type of the body extremity; and an area segmentation module that generates at least two segmented areas using the preset reference according to the type of the body extremity, wherein the body extremity type classification module acquires a boundary line for the body extremity using the body extremity image data and compares the average length of the branch parts with the average length of the base parts, to classify, according to the preset reference, the body extremity type into the hand or the foot.

2. The body extremity temperature change monitoring system as claimed in claim 1, wherein the image data acquisition unit comprises:

an image data acquisition module that acquires image data of the body extremity; and a thermal image data acquisition module that acquires thermal image data of the body extremity.

3. The body extremity temperature change monitoring system as claimed in claim 1, wherein when the type of the body extremity is the hand, the preset reference includes any one of 24-area segmentation, 32-area segmentation, and 5-line segmentation, and when the type of the body extremity is the foot, the preset reference includes any one of 19-area segmentation and 5-line segmentation.

4. The body extremity temperature change monitoring system as claimed in claim 2, wherein the body extremity temperature map generation unit comprises:

an image data merge module that generates merged image data by mapping the thermal image data to the image data including the segmented areas; and a body temperature distribution data generation module that generates the body extremity temperature map, which is temperature data for each segmented area, using the merged image data.

5. The body extremity temperature change monitoring system as claimed in claim 4, wherein the body extremity temperature map is acquired at a preset period to be generated to include time-series information.

6. The body extremity temperature change monitoring system as claimed in claim 1, further comprising a body temperature change analysis unit that observes a user's body temperature change using the body extremity temperature map and infers a user's state change according to the body temperature change using the preset reference.

7. The body extremity temperature change monitoring system as claimed in claim 6, wherein the body temperature change analysis unit comprises:

a body temperature change map generation module that calculates the user's body temperature change for a preset time using the body extremity temperature map and generates a body temperature change map using the body temperature change for each segmented area; and a state change inference module that compares a preset body temperature change reference with the body temperature change map to perform defining on the user's state change.

8. The body extremity temperature change monitoring system as claimed in claim 1, wherein the body extremity type classification module performs numbering or coloring for each of the segmented areas so that the segmented areas are distinguished from each other.

9. A body extremity temperature change monitoring method comprising:

an image data acquisition step of, by using an image data acquisition unit, acquiring body extremity image data that is image data of a body extremity including a hand and a foot;

a segmented area segmentation step of, by using a segmented area generation unit, segmenting the body extremity image data according to a preset reference to generate two or more segmented areas; and a body extremity temperature map generation step of, by using a body extremity temperature map generation unit, generating a body extremity temperature map using temperature data for each of the segmented areas, wherein the body extremity is defined to include base parts having a palm and a foot sole, and branch parts having fingers and toes, wherein the segmented area generation step comprises identifying a type of the body extremity; and generating two or more segmented areas using the preset reference according to the type of the body extremity, wherein in the step of identifying the type of the body extremity, a boundary line for the body extremity is acquired using the body extremity image data, and, according to the preset reference, the type of the body extremity is classified into the hand or the foot by comparing the average length of the branch parts with the average length of the base parts.

10. The body extremity temperature change monitoring method as claimed in claim 9, wherein the image data acquisition step comprises:

acquiring image data of the body extremity; and acquiring thermal image data of the body extremity.

11. The body extremity temperature change monitoring method as claimed in claim 9, wherein when the type of the body extremity is the hand, the preset reference includes any one of 24-area segmentation, 32-area segmentation, and 5-line segmentation, and when the type of the body extremity is the foot, the preset reference includes any one of 19-area segmentation and 5-line segmentation.

12. The body extremity temperature change monitoring method as claimed in claim 10, wherein the body extremity temperature map generation step comprises:

an image data merging step of generating merged image data by mapping the thermal image data to the image data including the segmented areas; and a body temperature distribution generation step of generating the body extremity temperature map, which is temperature data for each segmented area, using the merged image data.

13. The body extremity temperature change monitoring method as claimed in claim 12, wherein the body extremity temperature map is acquired at a preset period to be generated to include time-series information.

14. The body extremity temperature change monitoring method as claimed in claim 9, further comprising observing, by using a body temperature change analysis unit, the user's body temperature change using the body extremity temperature map, and analyzing the body temperature change by inferring a user's state change according to the body temperature change using the preset reference.

15. The body extremity temperature change monitoring method as claimed in claim 14, further comprising:

calculating the user's body temperature change for a preset time using the body extremity temperature map, and generating a body temperature change map using the body temperature change for each segmented area; and comparing the body temperature change map with a preset body temperature change reference to define a change in the user's state.

16. The body extremity temperature change monitoring method as claimed in claim 9, wherein each of the segmented areas is numbered or colored so that the segmented areas are distinguished from each other.

* * * * *